United States Patent
Del Vecchio

(10) Patent No.: US 10,799,633 B2
(45) Date of Patent: Oct. 13, 2020

(54) VIBRATIONAL DEVICE FOR FAT INSERTION DURING FAT TRANSPLANTATION

(71) Applicant: Lipovera, LLC, North Attleboro, MA (US)

(72) Inventor: Daniel A. Del Vecchio, Wrentham, MA (US)

(*) Notice: Subject to any disclaimer, the term of this patent is extended or adjusted under 35 U.S.C. 154(b) by 1098 days.

(21) Appl. No.: 13/897,866

(22) Filed: May 20, 2013

(65) Prior Publication Data
US 2013/0310749 A1   Nov. 21, 2013

Related U.S. Application Data

(60) Provisional application No. 61/649,488, filed on May 21, 2012.

(51) Int. Cl.
*A61M 5/20* (2006.01)
*A61B 17/32* (2006.01)
*A61B 17/00* (2006.01)

(52) U.S. Cl.
CPC ......... *A61M 5/20* (2013.01); *A61B 17/32002* (2013.01); *A61B 2017/00398* (2013.01); *A61B 2017/00969* (2013.01); *A61B 2217/005* (2013.01); *A61B 2217/007* (2013.01)

(58) Field of Classification Search
CPC .............. A61M 1/0039; A61M 1/0064; A61M 2205/106; A61B 17/32002; A61B 2217/005; A61B 17/320068
See application file for complete search history.

(56) References Cited

U.S. PATENT DOCUMENTS

| | | | | |
|---|---|---|---|---|
| 4,314,560 A | * | 2/1982 | Helfgott | A61F 9/00763 604/118 |
| 4,815,462 A | * | 3/1989 | Clark | A61B 17/32002 600/565 |
| 4,896,827 A | * | 1/1990 | Economou | A47G 29/1209 232/1 C |
| 5,002,538 A | * | 3/1991 | Johnson | A61J 1/2096 604/240 |
| 5,397,313 A | * | 3/1995 | Gross | A61M 5/31513 604/218 |

(Continued)

FOREIGN PATENT DOCUMENTS

WO   WO-2013177038   11/2013

OTHER PUBLICATIONS

Schubert, Werner, "Device for the Microfocal Generation of Mechanical Vibrations of the Low-Frequency Range, Even in Deeper Layers of the Body", DE_3439434A1. English and German Translations, Sep. 28, 2006, 54 pages.

(Continued)

*Primary Examiner* — William R Carpenter
(74) *Attorney, Agent, or Firm* — R. Keith Harrison

(57) ABSTRACT

An injection cannula includes a hand-held mechanical motorized device to improve delivery of fat and facilitate dispersion at a recipient site. The injection cannula may, for example be a cannula for injecting fat in a cosmetic surgical procedure for fat transplantation such as percutaneous injection or injection directly into the subcutaneous fat. An electric motor, pneumatic motor, or other mechanism may be used to provide vibration.

20 Claims, 1 Drawing Sheet

(56) References Cited

U.S. PATENT DOCUMENTS

| | | | | |
|---|---|---|---|---|
| 5,647,851 | A * | 7/1997 | Pokras | A61M 5/20 604/131 |
| 6,013,048 | A * | 1/2000 | Podany | A61B 8/546 604/22 |
| 6,258,054 | B1 * | 7/2001 | Mozsary | A61B 17/32002 604/22 |
| 6,379,326 | B1 * | 4/2002 | Cimino | A61M 1/0047 604/30 |
| 6,638,238 | B1 * | 10/2003 | Weber | A61B 17/32002 604/22 |
| 6,942,677 | B2 * | 9/2005 | Nita | A61B 17/22012 606/169 |
| 7,740,632 | B2 * | 6/2010 | Young | A61B 17/8822 606/92 |
| 2006/0206098 | A1 * | 9/2006 | Fard | A61M 1/0039 604/542 |
| 2006/0213374 | A1 | 9/2006 | Shippert | |
| 2006/0224144 | A1 * | 10/2006 | Lee | A61M 1/0009 604/542 |
| 2007/0032741 | A1 | 2/2007 | Hibner et al. | |
| 2007/0270771 | A1 * | 11/2007 | Ralph | A61B 17/1635 604/317 |
| 2009/0030438 | A1 * | 1/2009 | Stulen | A61B 17/320068 606/169 |
| 2010/0152614 | A1 * | 6/2010 | Mark | A61B 17/32002 600/567 |
| 2012/0035532 | A1 * | 2/2012 | Melsheimer | A61M 1/0064 604/28 |

OTHER PUBLICATIONS

Gazi, Bashir M., "Aperfeicoamentos Introduzidos Em Conjunto Instrumental Para Lipoaspiracao Por Vibracao De Pulsos, Aparelho, Dispositivos E Respectivo Equipamento De Controle", BRPI_0501122A. English and Spanish Translations, Oct. 17, 2006, 28 pages.

"International Application Serial No. PCT/US13/41819, Search Report and Written Opinion dated Sep. 24, 2013", 8 pages.

* cited by examiner

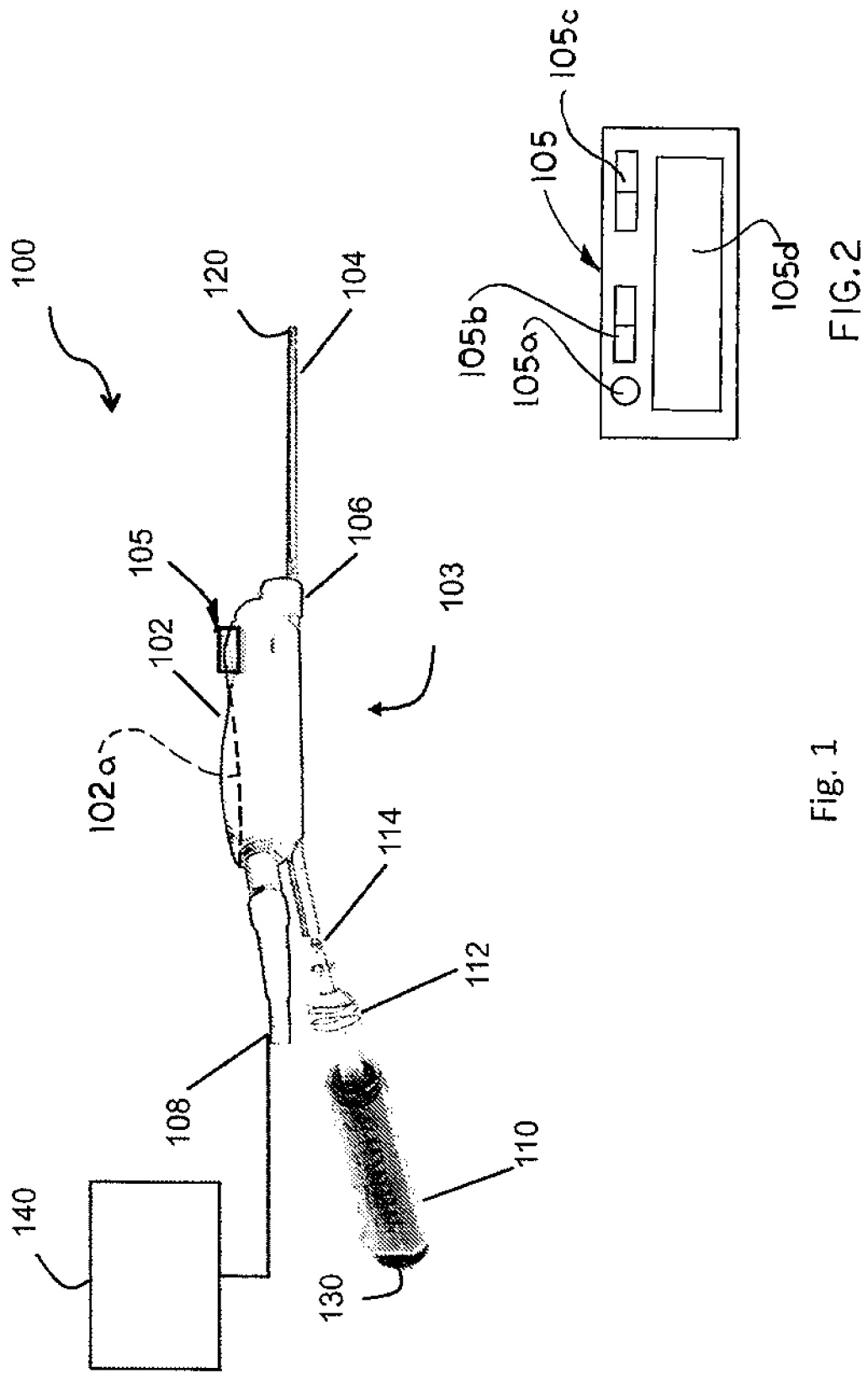

VIBRATIONAL DEVICE FOR FAT INSERTION DURING FAT TRANSPLANTATION

RELATED APPLICATIONS

This application claims the benefit of U.S. App. No. 61/649,488 filed on May 21, 2012, the entire content of which is hereby incorporated by reference.

BACKGROUND

Cannulas are surgical instruments, generally formed as tubes, used for delivery or removal of fluid and the like from a body. In cosmetic surgery, a cannula can be used to harvest fat or other tissue, and/or to inject fat or other tissue.

There remains a need for improved injection cannulas.

SUMMARY

An injection cannula includes a hand-held mechanical motorized device to improve delivery of fat and facilitate dispersion at a recipient site. The injection cannula may, for example be a cannula for injecting fat in a cosmetic surgical procedure for fat transplantation such as percutaneous injection or injection directly into the subcutaneous fat. An electric motor, pneumatic motor, or other mechanism may be used to provide vibration.

BRIEF DESCRIPTION OF THE FIGURES

The invention and the following detailed description of certain embodiments thereof may be understood by reference to the following figures:

FIG. 1 shows a hand-held mechanical motorized injection cannula device, and FIG. 2 shows a typical control for the motorized injection cannula device.

DETAILED DESCRIPTION

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus the term "or" should generally be understood to mean "and/or" and so forth.

Disclosed herein is a cannula connected to a hand-held mechanical motorized device for use in cosmetic surgical procedures such as all types of fat injection, including percutaneous injection or injection directly into the subcutaneous fat, during fat transplantation. However it will be understood that the invention disclosed herein is not so limited, and the inventive concept may be adapted to other tissue injection procedures or the like.

FIG. 1 shows a hand-held mechanical motorized injection cannula device. The device 100 may include a motor 102, an injection cannula 104, a connector 106, a motor power source connection 108, a syringe 110, a lock thread connector 112, and a syringe to hose connector 114.

The motor 102 may be shaped to be comfortably held by a user during all types of fat injection, including percutaneous injection or injection directly into the subcutaneous fat, during fat transplantation, or the vibrating motor 102 may be positioned away from a gripping portion 103 of the device 100 in any location suitable for transmitting vibrational forces to a tip 120 of the injection cannula 104. In general, the gripping portion 103 may be shaped and sized for gripping by a human hand, and more particularly for being held by a surgeon in any desired grip and orientation for a particular injection procedure.

The motor 102 may be constructed with a housing using, either individual r in combination, plastic materials, metals, or other appropriate material. The motor 102 may include vibration-absorbing materials 102a positioned between the motor 102 and the gripping, portion 103 to reduce the motor vibration transmitted to the user's hand, that is, to isolate vibrational forces between the motor 102 and the gripping portion 103 while at the same time being more directly mechanically coupled to the injection cannula 104.

The motor 102 may include a control 105 such as buttons, switches, slides, triggers, or other input control devices to allow the user to control the operation of the hand-held mechanical motorized injection cannula device 100. As illustrated in FIG. 2, by way of a non-limiting example, the vibration motor 102 may include a button 105a to turn the vibration motor 102 on and off, a slide switch 105b to control the motor speed, a slide switch 105c to control vibration amplitude, or other input control devices that may control the characteristics of the vibration motor 102. The control 105 may also include a display 105d to provide status information, an indication of vibrational intensity (rate and/or amplitude), or any other useful information.

In another aspect, the device 100 may include a pump 130 to actively control a delivery rate of fat or other material. This may include a thumb-operated plunger, or this may include any suitable electro-mechanical device for automatically delivering material at a controlled rate. In one aspect, the control 105 may include one or more buttons or the like to control a rate of delivery of material from the syringe 110.

The vibrating motor 102 may include any electric motor, pneumatic motor, or other electro-mechanical device that uses, e.g., an eccentricity or other mechanism to create vibration. Regardless of the type of motor 102, a power source 140 for the motor 102 may be connected at the motor power source connection 108. In one example, if the motor 102 uses an electric motor, the power supply connection 108 may include any suitable wires, plugs, and so forth. In another example, if the motor 102 uses an air compressor motor, a compressed air line may be connected to the motor power source connection 108. The compressed air line maybe connected using any typically available air line connector, such as, but not limited to, a quick connect/disconnect connector. In another aspect, the power source 140 may be integrated into the gripping portion 103 or other housing of the device 100 for independent operation of the device 100.

At an output of the motor 102, the injection cannula 104 may be connected to the motor 102 using the connector 106. The injection cannula 104 may be any needle typically used for fat or tissue injection procedures or the like. The connector 106 may be a twist type connector, Luer lock, or any other coupling that securely affixes the injection cannula 104 to the motor 102 and transmits vibrational energy from the motor to the injection cannula 104.

At the proximal end of the vibrating motor 102, a syringe 110 such as a Toomey syringe may be connected to the motor 102 using the locked thread connector 112 and the syringe to hose connector 114. In an embodiment, the syringe 110 may contain the fat or other tissue to be injected during a procedure. The syringe 110 may be coupled in fluid communication to the injection cannula 104 through the vibration motor 102 using a hose cannula or the like. The user may control the injection flow of fat or other tissue through the injection cannula 104 from the syringe 110 using, e.g., a thumb plunger or other automated or mechanical delivery system.

Depending upon the application, the injection cannula 104 may include a trocar or the like to facilitate injection. The tip 120 of the injection cannula 104 may also or instead include a sharpened point or other cutting surface to facilitate skin puncture.

In an embodiment, the device 100 may be used in fat injection, including percutaneous injection or injection directly into the subcutaneous fat, during fat transplantation. In a procedure using the device, a user can control injection or delivery rate of material in the syringe 110, and may concurrently control vibration characteristics of the motor for desired flow and distribution characteristics.

In an embodiment, the vibration characteristics of the vibrating motor 102 may be used to cause the injection cannula 104 to vibrate, and therefore may facilitate the flow of fat and egress of fat from the injection cannula 104 during fat injection, including percutaneous injection or injection directly into the subcutaneous fat, during fat transplantation. By way of a non-limiting example, while applying a steady pressure to the syringe 110, the user may increase the flow of fat or other tissue from the injection cannula 104 by increasing the vibration frequency of the vibrating motor 102. In another example, the user may increase the flow of fat or other tissue from the injection cannula 104 by increasing vibration amplitude of the vibrating motor 102.

In another embodiment, the hand-held mechanical motorized injection cannula device 100 vibration of the injection cannula 104 may facilitate the dispersion of fat into the recipient site during fat injection, including percutaneous injection or injection directly into the subcutaneous fat, during fat transplantation. By way of a non-limiting example, the vibration of the injection cannula 104 may move the tip of the injection cannula 104 within an increased space volume compared to a non-vibrating cannula, and therefore may disperse injected fat or other tissue into an increased uniform volume at the recipient site. As the user changes either the vibration frequency or the vibration amplitude, the space volume defined by movement of the tip 120 of the injection cannula 104 may change, resulting in a corresponding change in the injection space volume of the recipient site. Adjusting the vibration characteristics of the motor 102 may also control the flow and/or distribution of injected fat at a recipient site.

In an embodiment, the hand-held mechanical motorized injection cannula device 100 vibration of the injection cannula 104 may create a larger number of individual channels within a recipient site in which to disperse fat or other tissue, and therefore increasing the dispersion of fat grafts in all types of fat injection, including percutaneous injection or injection directly into the subcutaneous fat, during fat transplantation. As the user adjusts the vibration characteristics of the vibration motor 102 (vibration frequency or amplitude), the injection cannula 104 may create individual channels at the recipient site that are in proportion to the vibration characteristics of the vibration motor 102. As the user increases either the vibration frequency or amplitude, an increased number of individual channels at the recipient site may also be created in which fat or other tissue may be injected.

While particular embodiments of the present invention have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A device for vibratory injection of fat into a recipient site in a tissue to facilitate lipofilling of the tissue in a fat transplantation procedure, comprising:
   a gripping portion having a first end and a second end opposite the first end;
   a vibrating motor in the gripping portion between the first end and the second end;
   an injection cannula mechanically coupled to the vibrating motor at the first end of the gripping portion, the injection cannula having a cannula tip and the vibrating motor and injection cannula configured to transmit vibrational forces to the cannula tip of the injection cannula;
   a syringe connector at the second end of the gripping portion, the syringe connector coupled to the injection cannula through the gripping portion;
   a lock thread connector on the syringe connector;
   a syringe coupled to the lock thread connector in fluid communication with the injection cannula through the gripping portion at the second end of the gripping portion, the syringe is configured to both apply negative pressure to the fat in a negative displacement phase for suctioning of the fat through the injection cannula into the syringe through the gripping portion and apply positive pressure to the fat in a positive displacement phase for the injection of the fat from the syringe through the gripping portion and discharge of the fat from the injection cannula, respectively, as the vibrating motor vibrates the gripping portion; and
   a control controlling vibration of the vibrating motor, the control configured to facilitate selected adjustment in vibration frequency and vibration amplitude of the injection cannula as the fat is ejected from the syringe through the gripping portion and the cannula, respectively, into the recipient site in the tissue concurrent with application of the positive pressure to the fat in the positive displacement phase of the syringe, whereby vibration of the injection cannula is configured to move the cannula tip of the injection cannula within a selected space volume in the recipient site of the tissue to control and optimize flow and distribution of the fat in the recipient site and achieve an optimal combination of controlled dispersal of the fat in the tissue with maintaining cosmetic plumping and sculpting of the tissue.

2. The device of claim 1, further comprising fat contained within the syringe for use in a fat transplantation procedure.

3. The device of claim 1, wherein the motor is an electric motor.

4. The device of claim 1, wherein the motor is a pneumatic motor.

5. The device of claim 1, wherein the injection cannula facilitates the flow of fat and egress of fat from a tip of the injection cannula.

6. The device of claim 1 wherein the gripping portion is shaped and sized for a human hand.

7. The device of claim 1 wherein the motor is housed within the gripping portion.

8. The device of claim 7 further comprising a vibration-absorbing material between the motor and the gripping portion to isolate vibrational forces therebetween.

9. A device for vibratory injection of a fat including fat into a recipient site in a tissue to facilitate lipofilling of the tissue in a fat transplantation procedure, comprising:
- a generally elongated gripping portion having a first end and a second end opposite the first end;
- a vibrating motor in the gripping portion between the first end and the second end;
- a connector mechanically coupled to the vibrating motor at the first end of the gripping portion;
- an injection cannula mechanically coupled to the connector, the injection cannula having a cannula tip and the vibrating motor and injection cannula configured to transmit vibrational forces to the cannula tip of the injection cannula;
- a syringe connector at the second end of the gripping portion, the syringe connector coupled to the injection cannula through the gripping portion;
- a lock thread connector on the syringe connector;
- a syringe coupled to the lock thread connector on the syringe connector in fluid communication with the injection cannula through the vibrating motor at the second end of the gripping portion, the syringe is configured to both apply negative pressure to the fat in a negative displacement phase for suctioning of the fat through the injection cannula into the syringe through the gripping portion and apply positive pressure to the fat in a positive displacement phase for the injection of the fat from the syringe through the gripping portion and discharge of the fat from the injection cannula, respectively, as the vibrating motor vibrates the gripping portion; and
- a control controlling a vibration of the motor, the control configured to facilitate selected adjustment in vibration frequency and vibration amplitude of the injection cannula as the fat is ejected from the syringe through the gripping portion and the cannula, respectively, into the recipient site in the tissue concurrent with application of the positive pressure to the fat in the positive displacement phase of the syringe, whereby vibration of the injection cannula is configured to move the cannula tip of the injection cannula within a selected space volume in the recipient site of the tissue to control and optimize flow and distribution of the fat in the recipient site and achieve an optimal combination of controlled dispersal of the fat in the tissue with maintaining cosmetic plumping and sculpting of the tissue.

10. The device of claim 9 wherein the control is positioned on the gripping portion of the device.

11. The device of claim 9 wherein the control includes at least one of a button, a switch, and a slider.

12. The device of claim 9 wherein the control includes a display configured to provide information to a user relating to operation of the motor.

13. The device of claim 9 wherein the syringe comprises a pump for controllable delivery of the fat from the syringe into the injection cannula.

14. The device of claim 9 wherein the control includes a second control controlling a flow rate of fat from the syringe by the pump.

15. The device of claim 9 wherein the syringe includes a thumb plunger.

16. The device of claim 15 wherein the syringe includes a Toomey syringe.

17. A device for vibratory injection of a fat including fat into a recipient site in a tissue to facilitate lipofilling of the tissue in a fat transplantation procedure, comprising:
- a generally elongated gripping portion having a first end and a second end opposite the first end;
- a vibrating motor in the gripping portion between the first end and the second end;
- a connector mechanically coupled to the vibrating motor at the first end of the gripping portion;
- an injection cannula mechanically coupled to the connector, the injection cannula having a cannula tip and the vibrating motor and injection cannula configured to transmit vibrational forces to the cannula tip of the injection cannula;
- a syringe connector at the second end of the gripping portion, the syringe connector coupled to the injection cannula through the gripping portion;
- a lock thread connector on the syringe connector;
- a syringe coupled to the lock thread connector on the syringe connector in fluid communication with the injection cannula through the vibrating motor at the second end of the gripping portion, the syringe is configured to both apply negative pressure to fat in a negative displacement phase for suctioning of the fat through the injection cannula into the syringe through the gripping portion and apply positive pressure to the fat for the injection of the fat from the syringe through the gripping portion and discharge of the fat from the injection cannula, respectively, as the vibrating motor vibrates the gripping portion;
- a control controlling a vibration of the motor, the control configured to facilitate active control of vibration frequency and vibration amplitude of the injection cannula during a positive displacement phase of the syringe as the fat is ejected from the syringe through the gripping portion and the cannula, respectively, into the recipient site in the tissue concurrent with application of the positive pressure to the fat in the positive displacement phase of the syringe, whereby vibration of the injection cannula is configured to move the cannula tip of the injection cannula within a selected space volume in the recipient site of the tissue to control and optimize flow and distribution of the fat in the recipient site and achieve an optimal combination of controlled dispersal of the fat in the tissue with maintaining cosmetic plumping and sculpting of the tissue; and
- the syringe is removably and replaceably coupled to the syringe connector by a twist lock.

18. The device of claim 17 further comprising a power supply for the motor.

19. The device of claim 18 wherein the power supply includes a pressurized air supply.

20. The device of claim 18 wherein the power supply includes an electrical supply.

* * * * *